(12) United States Patent     (10) Patent No.:    US 9,078,642 B2
Vom et al.                                     (45) Date of Patent:      Jul. 14, 2015

(54) BIOLOGICAL SAMPLING DEVICE

(75) Inventors: Eduardo Vom, Fitzroy (AU); Craig Lewis, Eltham (AU); Richard Allman, Wyndham Vale (AU); Debbie Mantzaris, Avondale Heights (AU)

(73) Assignee: GENETIC TECHNOLOGIES LIMITED (AU)

( * ) Notice: Subject to any disclaimer, the term of this patent is extended or adjusted under 35 U.S.C. 154(b) by 635 days.

(21) Appl. No.: 13/146,376

(22) PCT Filed: Jan. 25, 2010

(86) PCT No.: PCT/AU2010/000071
§ 371 (c)(1),
(2), (4) Date: Nov. 9, 2011

(87) PCT Pub. No.: WO2010/085841
PCT Pub. Date: Aug. 5, 2010

(65) Prior Publication Data
US 2012/0122091 A1     May 17, 2012

Related U.S. Application Data

(60) Provisional application No. 61/147,718, filed on Jan. 27, 2009.

(51) Int. Cl.
*A61B 5/00*           (2006.01)
*A61B 10/02*         (2006.01)

(52) U.S. Cl.
CPC ..... *A61B 10/0291* (2013.01); *A61B 2010/0216* (2013.01)

(58) Field of Classification Search
CPC ............... A61B 10/0291; A61B 17/42; A61B 17/0218; A61B 18/1485; A61B 2010/0216; A61B 2017/4225
USPC .................................................. 600/564-572
See application file for complete search history.

(56) References Cited

U.S. PATENT DOCUMENTS

| 3,877,464 A | 4/1975 | Vermes |
| 3,995,636 A | 12/1976 | Murray et al. |

(Continued)

FOREIGN PATENT DOCUMENTS

| CN | 2134162 Y | 5/1993 |
| CN | 201171680 | 12/2008 |

(Continued)

OTHER PUBLICATIONS

International Search Report prepared by the Australian Patent Office on Mar. 31, 2010, for International Application No. PCT/AU2010/000071.

(Continued)

*Primary Examiner* — Max Hindenburg
(74) *Attorney, Agent, or Firm* — Sheridan Ross P.C.

(57) ABSTRACT

A sampling device adapted for transcervical sampling of biological materials from a pregnant patient comprising: an elongate insertion tube (4) having a first end (5) adapted for insertion through the external orifice (external os) of said patient's cervix and a second end (6) including a handle means (7) for manipulating said tube; a measuring means for determining the position of said first end of said tube within said cervix, wherein said first end (5) includes a sampling head (9, 14) adapted to collect biological material including cells, mucus and biological fluids, and wherein said measuring means is adapted to determine the extent of insertion and transcervical position of said first end to optimize the transcervical sampling site.

22 Claims, 9 Drawing Sheets

(56) References Cited

U.S. PATENT DOCUMENTS

| | | | |
|---|---|---|---|
| 4,194,513 | A | 3/1980 | Rhine et al. |
| 4,675,286 | A | 6/1987 | Calenoff |
| 4,681,123 | A | 7/1987 | Valtchev |
| 4,866,806 | A * | 9/1989 | Bedford ............... 15/104.94 |
| 4,988,617 | A | 1/1991 | Landegren et al. |
| 5,106,377 | A | 4/1992 | Martin |
| 5,242,794 | A | 9/1993 | Whiteley et al. |
| 5,494,810 | A | 2/1996 | Barany et al. |
| 5,916,175 | A | 6/1999 | Bauer |
| 5,954,670 | A | 9/1999 | Baker |
| 6,059,735 | A | 5/2000 | Sgro |
| 6,346,086 | B1 | 2/2002 | Maksem et al. |
| 6,582,938 | B1 | 6/2003 | Su et al. |
| 6,610,005 | B1 | 8/2003 | Tao |
| 6,749,576 | B2 | 6/2004 | Bauer |
| 6,969,585 | B2 | 11/2005 | Lorincz et al. |
| 7,087,028 | B2 | 8/2006 | Sak |
| 7,767,448 | B2 | 8/2010 | Yong |
| 8,343,072 | B2 | 1/2013 | Bacon et al. |
| 8,591,563 | B2 * | 11/2013 | Karpiel et al. ............... 623/1.11 |
| 8,734,364 | B1 | 5/2014 | Mantzaris et al. |
| 2003/0227611 | A1 | 12/2003 | Fein et al. |
| 2004/0126796 | A1 | 7/2004 | Carlson et al. |
| 2014/0073989 | A1 | 3/2014 | Vom et al. |

FOREIGN PATENT DOCUMENTS

| | | |
|---|---|---|
| EP | 0363196 A1 | 4/1990 |
| GB | 2126100 A | 3/1984 |

OTHER PUBLICATIONS

Written Opinion prepared by the Australian Patent Office on Mar. 31, 2010, for International Application No. PCT/AU2010/000071.

Adinolfi et al., "First trimester prenatal diagnosis using transcervical cells: an evaluation," Human Reproduction Update, 1997, vol. 3, No. 4, pp. 383-392.

Al-Mufti et al., "Investigation of Maternal Blood Enriched for Fetal Cells: Role in Screening and Diagnosis of Fetal Trisomies," Am. J. Med. Genet., 1999, vol. 85, pp. 66-75.

Bauer et al., "Paternity testing after pregnancy termination using laser microdissection of chorionic villi," Int. J. Legal Med., 2002, vol. 116, pp. 39-42.

Bischoff et al., "Endocervical fetal trophoblast for prenatal genetic diagnosis," Current Opinion in Obstetrics Gynecology, 2006, vol. 18, pp. 216-220.

Bulmer et al., "Immunohistochemical Characterization of Cells Retrieved by Transcervical Sampling in Early Pregnancy," Prenatal Diag., 1995, vol. 15, pp. 1143-1153.

Bussani et al., "Prenatal Diagnosis of Common Aneuploidies in Transcervical Samples Using Quantitative Fluorescent-PCR Analysis," Molecular Diagnosis & Therapy, 2007, vol. 11, Iss. 2, pp. 117-121.

Bussani et al., "Strategies for the isolation and detection of fetal cells in transcervical samples," Prenatal Diag., 2002, vol. 22, pp. 1098-1101.

Bussani et al., "Use of the Quantitative Fluorescent-PCR Assay in the Study of Fetal DNA from Micromanipulated Transcervical Samples," Mol. Diagn., 2004, vol. 8, pp. 259-263.

Cioni et al., "Fetal cells in cervical mucus in the first trimester of pregnancy," Prenatal Diag., 2003, vol. 23, pp. 168-171.

Fejgin et al., "Fetal cells in the uterine cervix: a source for early non-invasive prenatal diagnosis," Prenatal Diag., 2001, vol. 21, pp. 619-621.

Findlay et al., "Fluorescent polymerase chain reaction: Part I. A new method allowing genetic diagnosis and DNA fingerprinting of single cells," Hum. Reprod. Update, 1996, vol. 2(2), pp. 137-152.

Findlay et al., "Same day diagnosis of Down's syndrome and sex in single cells using multiplex flourescent PCR," J. Clin. Pathol. Mol. Pathol., 1998, vol. 51, pp. 164-167.

Findlay, I. et al., "Using MF-PCR to diagnose multiple defects from single cells: implications for PGD," Mol. Cell. Endocrin., 2001, vol. 183, pp. S5-S12.

Fitzgerald et al., "PCR Amplification of HIV and Cellular DNA Sequences in Formaldehyde-Fixed, Immunoreactive White Blood Cells," BioTechniques, 1993, vol. 15(1), pp. 128-133.

Goldberg et al., "First-trimester fetal chromosomal diagnosis using endocervical lavage: A negative evaluation," Am. J. Obstet. Gynecol., 1980, vol. 138, pp. 436-440.

Katz-Jaffe et al., "DNA identification of fetal cells isolated from cervical mucus: potential for early non-invasive prenatal diagnosis," BJOG, 2005, vol. 112, pp. 595-600.

Lehmann et al., "Real-Time PCR Analysis of DNA and RNA Extracted from Formalin-Fixed and Paraffin-Embedded Biopsies," Methods, 2001, vol. 25, pp. 409-418.

Mantzaris et al., "Preliminary report: correct diagnosis of sex in fetal cells isolated from cervical mucus during early pregnancy," Aus. NZ J. Obstet. Gynecol., 2005, vol. 45, pp. 529-532.

Massari et al., "Non-invasive early prenatal molecular diagnosis using retrieved transcervical trophoblast cells," Hum. Genet., 1996, vol. 97, pp. 150-155.

Miller et al., "Transcervical recovery of fetal cells from the lower uterine pole: reliability of recovery and histological/immunocytochemical analysis of recovered cell populations," Hum. Reprod., 1999, vol. 14(2), pp. 521-531.

Rhine et al., "A Simple Alternative to Amniocentesis for First Trimester Prenatal Diagnosis," Birth Defects Orig. Article Ser., 1977, vol. 12(3D), pp. 231-247.

Rhine et al., "Prenatal sex detection with endocervical smears: Successful results utilizing Y-body fluorescence," Am. J. Obstet. Gynecol., 1975, vol. 122, pp. 155-160.

Rodeck et al., "Methods for the Transcervical Collection of Fetal Cells During the First Trimester of Pregnancy," Prenatal Diag., 1995, vol. 15, pp. 933-942.

Shettles, "Use of the Y Chromosome in Prenatal Sex Determination," Nature, 1971, vol. 230, No. 5288, pp. 52-53.

Tutschek et al., "Isolation of Fetal Cells from Transcervical Samples by Micromanipulation: Molecular Confirmation of Their Fetal Origin and Diagnosis of Fetal Aneuploidy," Prenatal Diag., 1995, vol. 15, pp. 951-960.

Warren et al., "Prenatal Sex Determination from Exfoliated Cells Found in Cervical Mucosa," Am. J. Hum. Genet., 1972, vol. 24, No. 6, Pt. 1, p. 29a.

Official Action for U.S. Appl. No. 14/066,264 mailed Jan. 28, 2014, 9 pages.

Notice of Allowance for U.S. Appl. No. 14/074,215 mailed Jan. 14, 2014, 8 pages.

Notice of Allowance for U.S. Appl. No. 14/066,264 mailed May 6, 2014, 8 pages.

* cited by examiner

BIOLOGICAL SAMPLING DEVICE

CROSS REFERENCE TO RELATED APPLICATION

This application is a national stage application under 35 U.S.C. 371 and claims the benefit of PCT Application No. PCT/AU2010/000071, filed on Jan. 25, 2010, published as WO 2010/085841, which claims priority to U.S. Provisional Application No. 61/147,718, filed Jan. 27, 2009, the disclosure of both the above-identified applications are incorporated herein by reference.

FIELD OF THE INVENTION

This invention relates to a device and method for obtaining biological material and in particular, to a device and method for obtaining samples of fetal cells from pregnant females.

BACKGROUND OF THE INVENTION

Early prenatal diagnosis to detect fetal genetic disorders is desirable for both expectant mothers and physicians to make informed decisions. Definitive methods of invasive prenatal testing (amniocentesis and chorionic villous sampling) carry a small, but significant risk of miscarriage, and the results are rarely available before 13 weeks of pregnancy because of the time required for cell culture and analysis.

"Non-invasive" screening with maternal serum analyte screening and ultrasound can identify individuals at risk for fetal aneuploidy (predominantly trisomy 21), but a positive screening result still requires a subsequent invasive procedure for a definitive diagnosis. Of some 25-30 such procedures, only one will actually show a fetal aneuploidy.

Many laboratories around the world have been attempting for over a decade to develop non-invasive (i.e. venupuncture only) methods to isolate and analyse fetal cells. An obvious advantage is that definitive results can be obtained using molecular techniques such as fluorescence in-situ hybridization (FISH) and quantitative fluorescent polymerase chain reaction (QF-PCR) on recovered fetal cells.

The presence of fetal cells in maternal blood provides a possible source of cells for non-invasive prenatal diagnosis. However, fetal cells are present at very low numbers, and their isolation is not a trivial task, with only 1 or 2 fetal cells being present per 10 ml maternal blood. Evidence also indicates that the presence of intact fetal cells in the maternal circulation is not a universal event.

An attractive alternative to peripheral blood sampling is the isolation and analysis of trophoblasts from transcervical samples. Unlike maternal blood in which multiple circulating fetal cell types exist, fetal cells in the transcervical samples are all of placental origin and are overwhelmingly trophoblasts (Bischoff and Simpson, 2006).

It was long assumed that the cervical canal contained trophoblasts of fetal origin. The early embryo is covered with chorion levae, but later in the gestation the chorionic surface is smooth. However, it was not until 1971 that the presence of fetal cells in the endocervix was confirmed by identification of Y-chromosome bearing cells in midcervical mucous samples collected with a cotton swab (Shettles et al., 1971). Subsequent reports assumed that these fetal cells were shed from the regressing chorionic villous into the lower uterine pole (Warren et al., 1972, Rhine et al., 1975). In this scenario, it is most likely to occur between 7 and 13 weeks gestation, before fusion of the deciduas basalis and parietalis. Desquamated trophoblasts are believed first to accumulate behind the cervical mucous at the level of the internal opening section (Bulmer et al., 1995, Adinolphi and Sherlock, 1997) and then become ensconced in the cervical mucous.

These biologic events thus define the window of opportunity for endocervical sampling to be of use for prenatal diagnoses, although several studies have demonstrated trophoblast recovery as early as 5 weeks gestation (Katz-Jaffe et al., 2005, Mantzaris et al., 2005).

Efforts to extract trophoblasts were first made in the 1970's. Rhine et al. (1975 and 1977) described "antenatal cell extractors" that flush the endocervical canal with sterile saline to recover fetal cells. After culture, fetal metaphases from recovered cells were detected in approximately 50% of cases. However, other investigators reported negative results (Goldberg et al., 1980), leading to overall skepticism concerning clinical application. In hindsight, inability to detect fetal cells probably also reflected deficiencies in the clinicians' techniques in obtaining the endocervical specimen, as well as poor sensitivity of methods used to confirm the presence of fetal cells.

Interest was rekindled in the 1990's following the introduction of chorion villus sampling (CVS). A variety of techniques resulted in detection of fetal cells in 40-90% of specimens examined (Adinolfi et al., 1995a, Bussani et al., 2002, Cioni et al., 2003, Fejgin et al., 2001, Massari et al., 1996; Miller et al., 1999; Rodeck et al., 1995; Tuttschek et al., 1995). Again, however, interest waned in most centres because analysis was difficult. The presumptive fetal cells embedded in mucous were not readily amenable to FISH. More recently, molecular PCR techniques for micromanipulated cell clumps of trophoblastic origin were demonstrated to have utility for transcervical samples (Bussani et al., 2004; Bussani et al., 2007; Katz-Jaffe et al., 2005).

Most transcervical specimens contain a variety of maternally derived cells (leukocytes, macrophages, squamous epithelia, columnar epithelia, and endocervical cells) as well as different fetal-derived cells (cytotrophoblasts and syncytiotrophoblasts) (Bulmer et al., 1995, Miller et al., 1999). The frequency of each fetal cell type is variable and seemingly dependent on the collection method and gestational age.

A range of devices designed to access the cervical region including cotton and/or other swabbing or sampling spatulas, aspirating devices, and lavange techniques for flushing to obtain samples etc are currently available. However, all the prior art devices to date are designed for use on non-pregnant females and fail to provide fetal cell samples of reliable quality from pregnant female patients; including the concentration of fetal cells, consistency of sample collection; plus, ease of use and consideration of patient/fetus safety to a standard sufficient to challenge the reliability, albeit with the associated clinical risks, of amniocentesis and chronic villous sampling.

There is a need for a device adapted for sampling biological material from pregnant females, particularly for obtaining transcervical samples comprising fetal cells.

SUMMARY OF THE INVENTION

In a first aspect the invention provides a sampling device adapted for transcervical sampling of biological materials from a pregnant patient comprising:
- an elongate insertion tube having a first end adapted for insertion through the external orifice (external os) of said patient's cervix and a second end including a handle means for manipulating said tube;
- a measuring means for determining the position of said first end of said tube within said cervix wherein said first end includes a cell sampling head adapted to collect biological material including cells, mucus and biological fluids, and wherein said measuring means is adapted to determine the extent of insertion and transcervical position of said first end to optimise the transcervical sampling site.

The measuring means may include a physical stop, a physical scale and/or an ultrasound or similar means for determining the in situ position of said head.

The sampling head is preferably adapted to collect or capture a quantity of biological material available from within the patient's cervix including mucous, blood, tissue and cells per se. The capture preferably includes adsorption of biological material onto the surface of said head but may include absorption of biological material into the head.

The sampling head preferably includes a compliant, soft (may not be soft initially) and absorptive sponge, or sponge-like material adapted to retain a soft feel in the compressed pre-absorptive state and may be chosen from a range of materials including polyvinyl acetate (PVA), polyurethane (PU) and cellulose. The sponge or sponge-like material may be selected from any one or a combination of:

1. Fabric dressing, non-woven. Either polyester, rayon, cotton or blend of these.
2. Hydrocolloid foam, approximate pore size 200-300 μm.
3. Polyurethane, ~100% open cell. Approximate pore size 500-600 μm.
4. Cellulose sponge, similar fine pore size to Merocel PVA spears.
5. PVA cylinder. Fine pore size, 90-120 μm. Sides of cylinder are smooth, almost appear closed.
6. Cellulose sponge, layered construction. Combination of fine pores within the layer, and large pores (>500 μm) between layers.
7. PVA sponge, supplied compressed in single dimension, random pore size (between ~250 and 700), comes attached to drawstring.

The sampling head may also optionally be formed of hydrophilic materials and the outer surface of the sampling head, may be shielded with the temporary cover or chemical coating. The shield allows the user to selectively control the point at which the sampling head is exposed and commences collecting biological material, including the ability of the temporary cover or coating to protect the sampling head during insertion such that the temporary cover or coating can be removed only when the sampling head is correctly positioned within the cervix.

The shield may be a dissolvable chemical coating or membrane applied to the outer surface of the head, where the chemical coating or membrane is adapted to dissolve over a finite period of time, allowing the sampling head to be inserted without risk of contamination by collecting biological material during the insertion process.

As an alternative, the shield may take the form of a physical barrier of an outer sleeve which is adapted to cooperate coaxially with the insertion tube such that the insertion tube is inserted telescopically within the outer sleeve and the relative movement of the sampling head (and associated insertion tube) with the outer sleeve provides for movement between a first retracted position where the sampling head is fully contained within and protected within the confines of the outer sleeve and a second extended position where the sampling head has been telescopically moved out and away from the outer sleeve and is then exposed for sample collection.

As another alternative, the "shield" may be effected by the pre-use compression of the sponge-like head so as to delay sample collection until the sample head has expanded in situ.

The sampling device preferably includes a stop means which can take the form of a first stop adapted to cooperate with the outer sleeve so as to provide a setting means or stop to allow the user to judge the extent of insertion of the sleeve into the patient's cervix. The first stop would be adapted to gently abut the exterior os of the patient's cervix, thereby allowing the patient to carefully judge the extent of insertion of the outer sleeve into the interior of the patient's cervix.

The stop means may form part of the measuring means of the device.

The insertion tube may also include it's own stop in the form of a second stop to allow control of the telescopic movement and extension of the sampling head, relative to the outer sleeve.

The sampling head is preferably adapted to expand upon absorption of the sample and expand from a dry compressed state to a swollen state having absorbed and holding the sample.

The sampling head is most preferably configured to provide a high surface area to volume ratio in order to maximise the adsorption of mucus onto the surface of the head. In another embodiment, the head adopts a radially expanded swollen state where the sampling head preferentially expands in a radial direction upon contact with the sampling site and absorption of the sample.

The sampling site of interest for optimal collection of fetal cells is between the internal os and the external os of the patient; but most preferably closer to the internal os of the patient's cervix (when compared to the external os), where the internal os is defined as the internal orifice of the uterus being an interior narrowing of the uterine cavity corresponding to a slight constriction known as the isthmus that can be observed on the surface of the uterus about midway between the apex and the base.

The absorptive materials in the sample head preferably include a pore size between 10 to 2000 microns with an average pore opening between 400 to 1000 microns. The pore size is preferably configured so that it does not diminish toward the outer surface of the sample head in order to ensure that absorption and in particular adsorption of the sample head is not blocked or constrained by the initial absorption from the surface of the sample head.

Most preferably, the sample head is shaped such that the surface area to volume ratio is the same as, or increased, compared to that of a cylindrical shaped sample head. The sampling head is preferably configured as a multifilamentous array of sponge or sponge-like fingers. The sample head may alternatively be shaped as a cylinder with the cylinder optionally including a hollow for the addition of an optional aspirating means. The preferential overall size of the sampling head in its compressed form, being about 3 mm in diameter and allowing an expansion between 5 to 20 mm once the predetermined quantity of biological material has been collected.

The sampling head preferably has a length between 1 to 5 cm prior to collecting said sample and an expanded volume at the predetermined optimal volume between 0.5 to 3 cubic centimeters. The expansion is preferably radial.

The predetermined quantity of biological material absorbed or adsorbed by the sampling head is preferably between 0.01 ml and 3 ml but will depend on the nature and condition of the patient.

The insertion tube of the sampling device preferably includes markings along the length thereof adapted to cooperate with the stop means and provide a quantitative measure for the extent of insertion and ultimately the transcervical position of said sampling head once the device is fitted. The outer sleeve when fitted to the device, is preferably provided with markings along the length thereof to cooperate with a second stop and provided quantitative measure of the extent of insertion and the transcervical position of the sampling head.

In addition, the elongate tube and/or the cell sampling head may include an ultrasound readable marker to assist in tracing the inserted position of the sampling head within the patient using ultrasound monitoring.

The outer sleeve, if incorporated into the sampling device may also include an ultrasound readable marker to assist in tracing the position of the sampling head relative to the outer sleeve within the patient.

The sampling device may optionally include an aspirating means including a vacuum generating means. The sampling device when incorporating the optional aspirating means may integrate same with the outer sleeve component thereof which can be adapted to transfer the vacuum as applied to the device to the sampling head.

The sampling device of the invention may optionally include a sample storage means and/or transport means to allow the sample to be preserved and stored in a suitable manner to allow transport without the need for transferral thereby maximising preservation of the sample.

In an embodiment, said sampling head is adapted for removal from said device and integration with a transport container or the like such that said integrated transport device maintains the sterility and integrity of said sample. For example, a snap fit feature is moulded into the middle of the lid of the transport container or the like such that the sampling head can be snap fitted into the feature for transport. The transport container or the like may also comprise a suitable media into which the sampling head can be submerged.

In another aspect the invention provides a method of sampling biological material from a patient comprising the steps of:
 introducing a sampling device into said patient;
 inserting a sampling head into the internal os region of said patient's cervix;
 taking a cell sample from said internal os region;
 withdrawing said sampling head from said patient and harvesting collected biological material.

The method of the invention is preferably exercised using the sampling device as previously described.

The method of the invention may comprise the steps of:
 measuring the cervical canal length of said patient;
 adjusting the stop means of said device to position said sampling head at or near the internal os region of said patient's cervix;
 inserting said device;
 leave said sampling head in said patient until the required or predetermined quantity of said biological material is collected;
 removing said device and harvesting collected biological material.

In order to maximise the collection of biological material from the primary target site, the method of the invention preferably utilises the device of the invention as previously described incorporating a protective shield and outer sleeve telescopically cooperating with the sampling head whereby the method comprises steps of:
 measuring the cervical canal length of said patient;
 adjusting the first stop and second stop of a sampling device as previously described to position said cell sampling head at or near the internal os region of said patient when at that point the sampling head can be extended out of the protective outer sleeve;
 the device is inserted to position the first stop at the patient's external os;
 the insertion device is extended to the second stop thereby moving the sampling head out of the outer sleeve to the internal os region;
 the sampling head is left in the extended position until the required or predetermined quantity of biological material is collected;
 the device is then removed and the biological material harvested.

In another variation of the method previously described:
 the cell sampling head is positioned at or near the internal os region of the patient whilst still protected by the shield of the outer sleeve
 the device is then inserted to position the first stop at the patient's external os,
 the outer sleeve is then retracted relative to the sampling head whilst maintaining the position of the sampling head so as to expose the sampling head for collection at the highly specific internal os region,
 the sampling head is then left in this position until the required or predetermined quantity of biological material is collected and is then removed and the biological material harvested for collection.

In an embodiment, the biological material obtained using a method of sampling the invention comprises fetal cells.

In another aspect of the method, the cervical length of the patient can be determined either by a patient's knowledge of their own anatomy or by measuring or monitoring the resistance as a device is inserted. Once the cervical length of the patient is known, the device can be inserted in accordance with the above determination near the interior os region of the patient's cervix. The sampling head is left in situ until the sample is collected which can be over a period of between 1 second to 10 minutes or up to 48 hours as required and then the device is removed and the collected biological material is harvested. The absorbing time can be between 1 second to 10 minutes with the duration the device is left in the cervix between 30 seconds and two days.

In another aspect, the present invention provides a method for analysing the genotype of a fetal cell at a locus of interest, the method comprising
 i) obtaining fetal cells using a method of the invention, and
 ii) analysing the genotype of at least one fetal cell at a locus of interest.

The genotype of the fetus can be determined using any technique known in the art. Examples include, but are not limited to, karyotyping, hybridization based procedures, and/or amplification based procedures.

The genotype of a fetal cell can be analysed for any purpose. Typically, the genotype will be analysed to detect the likelihood that the offspring will possess a trait of interest. Preferably, the fetal cell is analysed for a genetic abnormality linked to a disease state, or predisposition thereto. In one embodiment, the genetic abnormality is in the structure and/or number or chromosomes. In another embodiment, the genetic abnormality encodes an abnormal protein. In another embodiment, the genetic abnormality results in decreased or increased expression levels of a gene.

In at least some instances, the methods of the invention will not result in a pure fetal cell population. In other words, some maternal cells may remain. Thus, in a preferred embodiment the methods of diagnosis (determination, analysis etc) further comprises identifying a cell as a fetal cell.

The enriched/detected fetal cells can be used to determine the sex of the fetus. As a result, in a further aspect, the present invention provides a method of determining the sex of a fetus, the method comprising
  i) obtaining fetal cells using a method of the invention, and
  ii) analysing at least one fetal cell to determine the sex of the fetus.

The analysis of the fetal cells to determine the sex of the fetus can be performed using any technique known in the art. For example, Y-chromosome specific probes can be used, and/or the cells karyotyped.

The enriched fetal cells can also be used to identify the father of the fetus. Accordingly, in a further aspect, the present invention provides a method of determining the father of a fetus, the method comprising
  i) obtaining fetal cells using a method of the invention,
  ii) determining the genotype of the candidate father at one or more loci,
  iii) determining the genotype of the fetus at one or more of said loci, and
  iv) comparing the genotypes of ii) and iii) to determine the probability that the candidate father is the biological father of the fetus.

Whilst in some cases it may not be essential that the genotype of the mother also be analysed, for accuracy it is preferred that the method further comprises determining the genotype of the mother at one or more of said loci.

Analysis of the genotype of the candidate father, fetus or mother can be performed using any technique known in the art. One preferred technique is performing DNA fingerprinting analysis using probes/primers which hybridize to tandemly repeated regions of the genome. Another technique is to analyse the HLA/MHC region of the genome.

The device of the invention is also useful for obtaining pap smears. Accordingly, in a further aspect the present invention provides a method for the diagnosis, prognosis, and/or prediction of therapeutic outcome of a cervical cancer, the method comprising obtaining biological material from the cervix of a patient using the device of the invention, and analysing the biological material for cervical cancer cells or a marker thereof.

In another aspect, provided is a kit comprising a sampling device of the invention.

Preferably, the patient is a mammal such as, but not limited to, humans, livestock animals such as sheep, cattle and horses, as well as companion animals such as cats and dogs. In a particularly preferred embodiment, the patient is a pregnant female human, however, in the case of obtaining a pap smear the patient does not have to be pregnant.

The device may be used at any stage of pregnancy. Preferably the sample is obtained during the first and second trimester of pregnancy. More preferably, the sample is obtained in the first trimester of pregnancy. Ideally the sample is obtained at a stage when a decision can be made for the well-being of the fetus and preferably within a period where an opportunity to make an early decision regarding therapeutic abortion can be made. Preferably, the sample is obtained up to 14 weeks of the pregnancy.

As will be apparent, preferred features and characteristics of one aspect of the invention are applicable to many other aspects of the invention.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

BRIEF DESCRIPTION OF THE DRAWINGS

FIG. 2a shows a close-up of the sampling head of the insertion member of FIG. 2.

DETAILED DESCRIPTION OF THE INVENTION

General Techniques and Definitions

Unless specifically defined otherwise, all technical and scientific terms used herein shall be taken to have the same meaning as commonly understood by one of ordinary skill in the art (e.g., in cell culture, fetal cell biology, molecular genetics, immunology, immunohistochemistry, protein chemistry, nucleic acid hybridization, flow cytometry, and biochemistry).

Unless otherwise indicated, the recombinant protein, cell culture, and immunological techniques utilized in the present invention are standard procedures, well known to those skilled in the art. Such techniques are described and explained throughout the literature in sources such as, J. Perbal, A Practical Guide to Molecular Cloning, John Wiley and Sons (1984), J. Sambrook et al., Molecular Cloning: A Laboratory Manual, Cold Spring Harbour Laboratory Press (1989), T. A. Brown (editor), Essential Molecular Biology: A Practical Approach, Volumes 1 and 2, IRL Press (1991), D. M. Glover and B. D. Hames (editors), DNA Cloning: A Practical Approach, Volumes 1-4, IRL Press (1995 and 1996), and F. M. Ausubel et al. (editors), Current Protocols in Molecular Biology, Greene Pub. Associates and Wiley-Interscience (1988, including all updates until present), Ed Harlow and David Lane (editors) Antibodies: A Laboratory Manual, Cold Spring Harbour Laboratory, (1988), and J. E. Coligan et al. (editors) Current Protocols in Immunology, John Wiley & Sons (including all updates until present).

As used herein, the term "transcervical sample" refers to material taken directly from the pregnant female comprising cervical mucous, as well as such material that has already been partially purified. Examples of such partial purification include the removal of at least some non-cellular material, removal of maternal red blood cells, and/or removal of maternal lymphocytes. In some embodiments, the cells in the sample are cultured in vitro before a method of the invention is performed.

As used herein, the term "internal os" refers to the internal orifice of the uterus being an interior narrowing of the uterine cavity corresponding to a slight constriction known as the isthmus that can be observed on the surface of the uterus about midway between the apex and the base.

Sampling Device

Figure 1:
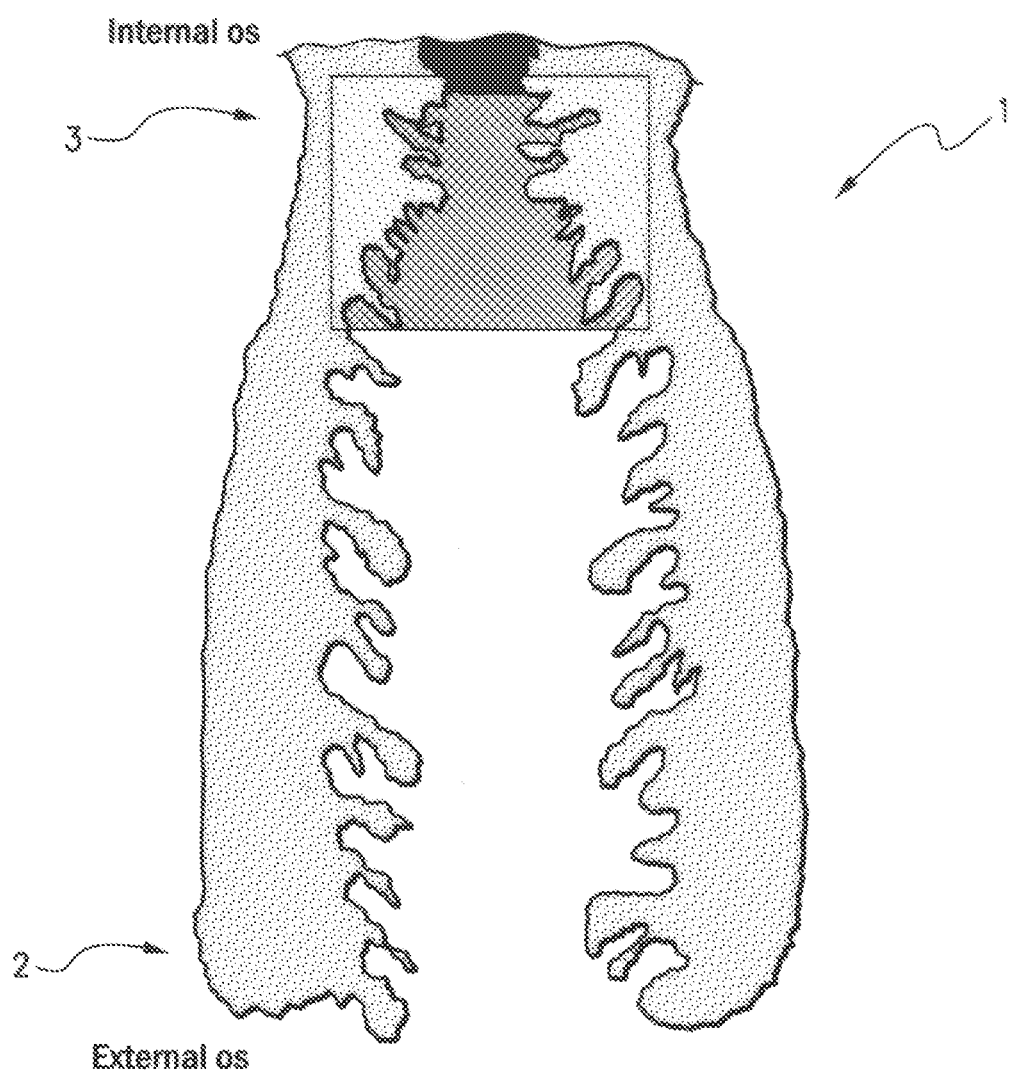
FIG. 1 shows a schematic rendering of the front portion of the human cervix.

The sampling device and methods of the invention will now be described with reference to the particular embodiments as detailed in FIGS. 1 through to 11:

FIG. 1 provides a schematic rendering of the front portion of the human cervix 1, with the entry to the cervix occurring at the external os 2 and the neck of the cervix drawing in to the internal os region 3 within the body of the cervix.

The invention is concerned with the recognition of the internal os region of the cervix as providing an optimal site for collection of biological material which represent a valuable diagnostic and analytical tool.

Figure 2:
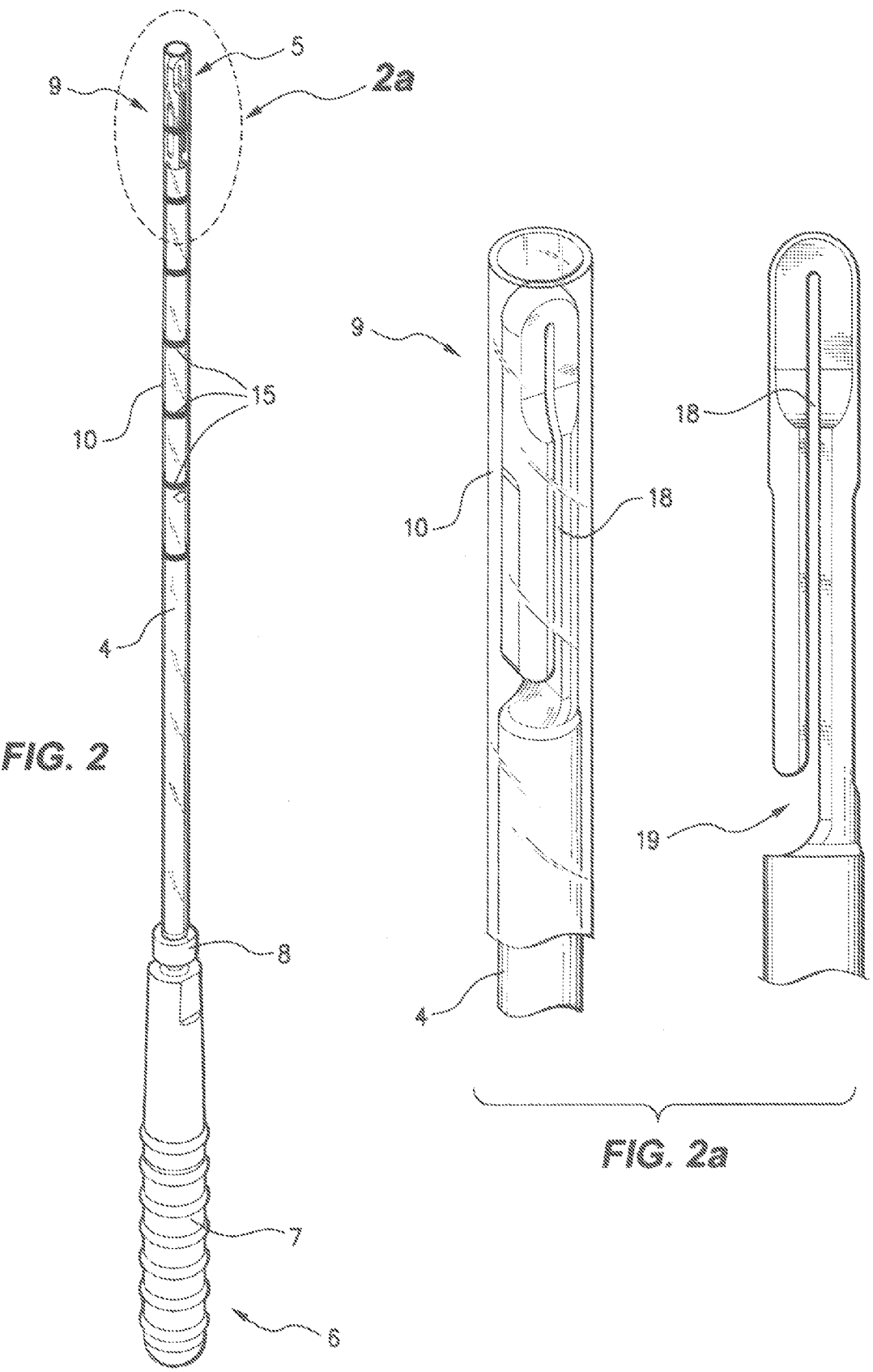
FIG. 2 shows a lengthwise view of the insertion tube of the sampling device according to some embodiments.

The first aspect of the invention relates to the provision of a sampling device developed for this specific purpose of allowing the user a high degree of control over the sampling methodologies and techniques with a particular emphasis on allowing the user to access a biological sample from the internal os region of the cervix. In its simplest form, the sampling device of the invention is represented in FIG. 2 and comprises an elongate insertion tube 4 which can take the form of a hollow cylindrical tube, solid tube or any other form of elongate vehicle allowing access to the interior of the cervix. The elongate insertion tube 4 has at a first end 5, a sampling head 9 which is adapted for insertion into the external os of the patient's cervix and a second end 6 having a handle means 7 allowing the user to manipulate and operate the device by careful insertion into the cervix. The elongate tube includes a sampling head 9 where the head preferably includes a terminal hook forming a slot 18 with an opening 19 for inserting a compliant and absorptive sponge like material preferably having a structure of substantially open cell porous characteristics. The sampling device is further provided with a measuring means in the form of a stop means 8 being a collar adapted for positioning along the length of the elongate tube 4 where the stop means is sized and configured to carefully abut the external os of the cervix during insertion wherein the movement of the stopper means 8 along the length of the elongate tube in accordance with a series of longitudinal markings 15 allows the user to insert the sampling device into the cervix for a specific distance. The distance between the stopper means and the sampling head is carefully measured to correlate with the position of the internal os of the cervix of the patient. In this manner, the sampling device can be specifically configured for each individual patient by setting the stopper means to the appropriate distance, thereby ensuring that the cell sampling head has access to the optimal sampling region of the internal os of the patient.

The sampling head is most preferably formed of or include an absorbent material which is capable of being formed into an open cell foam or sponge configuration providing a level of compliance in the virgin state so as to ensure that the insertion of the sampling device into the cervix does not abrade, tear or in any way damage the lining of the cervix prior to absorption of the sample from the internal os region, whereby the sampling head will expand and soften due to the absorption of biological fluids associated with the cell sampling. The absorbent material may be selected from polyvinyl acetate, polyurethane, cellulose or any other suitable absorbent material and is preferably provided in a manner such that small pieces or fibres of the sampling head will not shed at any stage during the sampling procedures. The open cell material of the porous head is substantially porous having preferably about 90% of open cells are most preferably including 100% open cells. The sampling head materials are preferably hydrophilic with materials most preferably chosen that are hydrophilic in an untreated state. Alternatively, the sampling head absorbent materials may be treated so as to alter the surface energy or polarity including plasma or chemical treatment methods.

The sampling head is most preferably configured to provide maximum capture of mucal biological material by adsorption onto the surface of the collection head. In particular, the sampling head is preferably configured to maximise the surface area for adsorption of mucus and a configuration as a multifilamentous array of sponge or sponge-like fingers as detailed in FIG. 3 form as one particularly preferred embodiment of the invention.

The pore size of the sampling head material is preferably sized between 10 to 2000 microns with an average pore opening over the whole sampling head of between 400 to 1000 microns. The distribution of pore size throughout the sampling head could be consistent or random in accordance with the particular requirements to which the sampling device may be applied. The outer surface of the sampling head is preferably configured such that the outer pores of the sampling head are no smaller than the pore size throughout the absorptive material of the sampling head so as to ensure that the outer or surface pores of the sampling head are not closed off or permanently filled or coated upon access to the sampling site in a manner that may reduce the ability of the sampling head to rapidly and efficiently absorb the sample. The sampling head absorption characteristics may be configured to provide a fixed and predetermined quantity of absorptive capacity so as to allow the sampling device of the invention to absorb and adsorb a known and predetermined quantity of liquid and mucus beyond which no further biological material will be absorbed. In this manner, the sampling device of the invention can be used in a manner ensuring that only the most relevant sample is collected from the internal os region and the risk or chance of contamination of the sampling head with further absorption of cells from other regions of the cervix as the sampling head is withdrawn from the patient are minimised.

In addition, the outer surface of the sampling head may be coated with a temporary coating to delay absorption. Such a dissolvable substance or material can be used with a time delay function such that the outer surface coating of the sponge is dissolved after insertion of the sampling head into the cervix and with sufficient delay to allow the sampling head to be correctly positioned at the optimal point at the internal os. In this manner, the absorptive function of the sampling head will be protected from premature absorption during insertion through the cervix.

Figure 3:
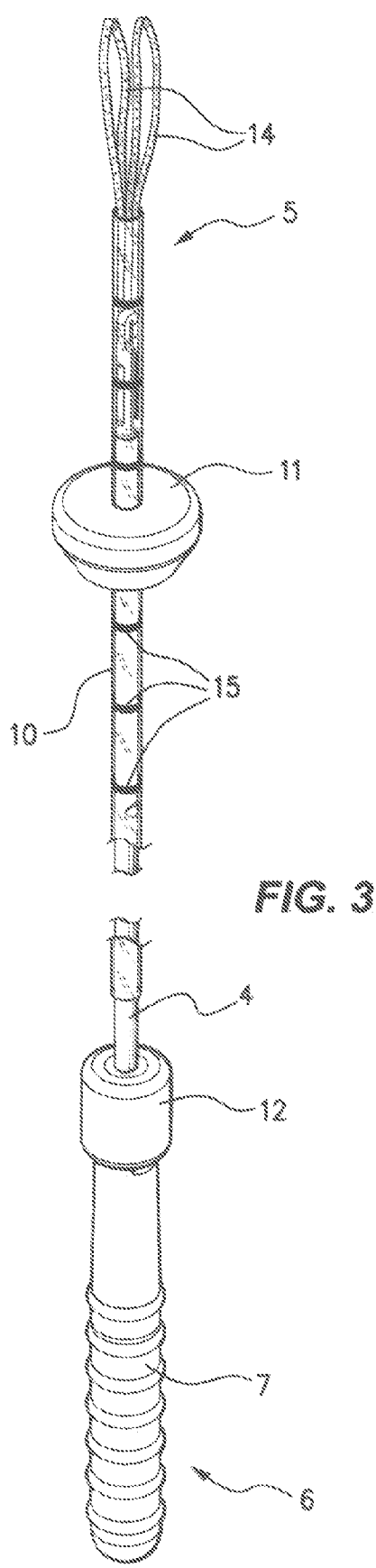
FIG. 3 shows a sampling device according to some embodiments in which the sampling head is configured as a multifilamentous array of sponge or sponge-like fingers.
Figure 4:
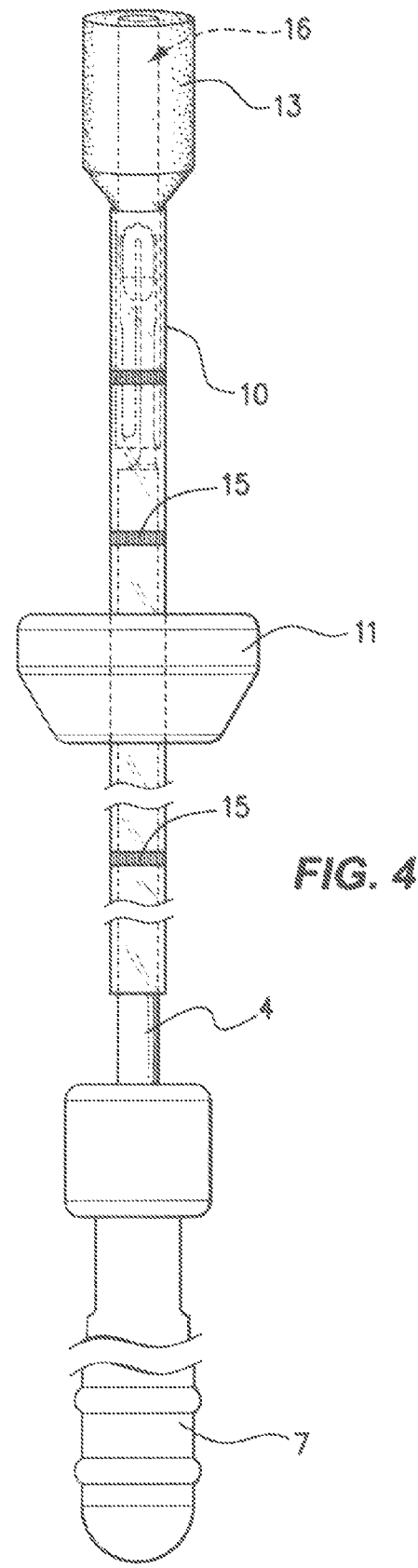
FIG. 4 shows a sampling device according to some embodiments in which the sampling head has a cylindrical shape.

The form of the sampling head can be configured to adopt a wide range of shapes including general cylindrical shapes as shown in FIG. 4, wherein the ratio of surface area to volume is at least equal to that of a cylinder or increased compared to a cylinder in this manner the mucous and cell samples can be absorbed onto the sponge pores and also held by the surface and between the surfaces of the sponge pores. The surface collection of the sponge also allows for the collection of clumps or aggregations of samples or other biological material larger than the actual pore size particularly mucus which is adsorbed onto the surface. The ratio of surface area to volume, can be increased when using the cylindrical configuration by the provision of slots or the use of multiple pieces of foam or sponge as strips 14 as shown in FIG. 3. The most preferred biological material as a source of fetal cells is mucus which has been found to collect most effectively by adsorption onto the surface of the sampling head and absorption into the interior of the sponge. In this manner the highest surface area to volume ratio as provided by a multifilamentous array of sponge or sponge-like fingers as shown in FIG. 3 provides one of the most preferred embodiments for effectively sampling biological material as provided by the invention.

FIG. 4 shows a cylindrical embodiment of the sponge head 9 in the form of a hollow sponge 13 where the cavity 16 can allow the sampling device to incorporate an aspiration function.

Figure 5:
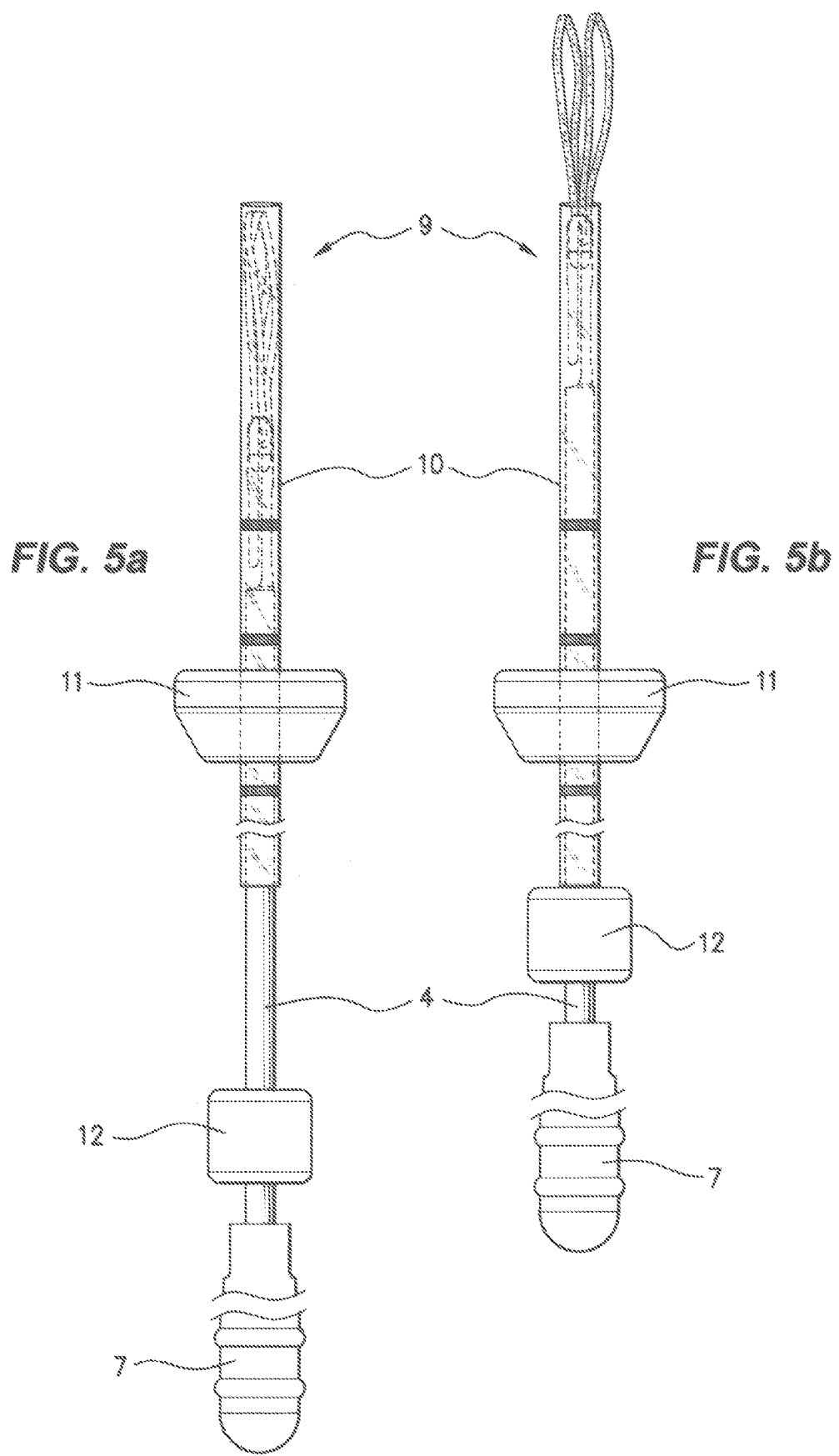
FIG. 5a shows a lengthwise view of the sampling device of FIG. 3 in a first position.
FIG. 5b shows a lengthwise view of the sampling device of FIG. 3 in a second position.

Referring now to FIGS. 3, 4 and 5 in more detail, the sampling device of the invention may be provided with an outer sleeve 10 adapted for telescopic cooperation with the elongate tube 4 moving within the longitudinal length of the outer sleeve. In this manner the elongate tube and sampling head can be moved between a first retracted position as shown in FIG. 5*a*, whereby the sampling head is fully contained and protected within the confines of the outer tube or sleeve 10 and a second extended position where the elongate tube 4 is pushed telescopically through the outer sleeve 10 by pushing the handle 7 relative to the outer sleeve so as to project the sample head out beyond the outer sleeve as shown in FIG. 5*b*. In this embodiment of the invention, the stop means most preferably includes a first stop 11 adapted to cooperate with the outer sleeve 10 by movement up and down the length of the outer sleeve and a second stop 12 adapted for movement up and down the length of the elongate tube 4 so as to provide this embodiment of the device with a two stage action where the combined use of the first and second stop allows the final position of the sampling head, once extended from the outer sleeve 10, to be accurately positioned at the internal os of the patient's cervix. The first stop 11 is adapted for movement or setting along the length of the outer sleeve in accordance with appropriate markings 15, which allow the insertion of the device to be specifically limited to a maximum depth as the first stop 11 gently abuts the external os of the patient's cervix. The first and second stops could be formed as a collar and can be made of rubber, plastic or other suitable materials having an interference fit with the outer sleeve 10 and elongate tube 4 respectively, such that they can be readily moved up and down to the appropriate depth in accordance with the physiology of the patient. The use of the first stop and second stop allows a variety of uses of the device of the invention, including the introduction of the outer sleeve 10 into the cervix at a point forward of the internal os in accordance with the first stop 10 wherein the second stop 12 could be positioned in the elongate tube 4 such that once the device is inserted into the cervix, the elongate tube can be moved to the second extended position so as to progress the insertion of the sampling head up to the optimal position of the internal os whereby the second stop 12 would ensure that the sampling head is stopped at the precise position within the patient's cervix.

The positioning of the stop means can be set by the patient's practitioner using knowledge of the cervical length gained from ultrasound or other techniques. In a particularly preferred embodiment, the tip of the elongate tube and/or outer sleeve may be coated or impregnated with a material clearly visible using ultrasound. Such a material could include silver, with antibacterial properties. In this manner, the device of the invention could be readily calibrated for each patient thereby ensuring optimal precision and insertion for sample collection at the internal os of each particular patient.

The configuration of the sampling head of the device is preferably designed to maximise absorption from the optimal region of the internal os and most preferably has a prior absorptive length of between 0.5 to 5 cm with an expanded volume at set predetermined volume of between 0.01 to 3 cubic cm. The preferred predetermined quantity of said cells or sample can be set between 0.01 ml and 3 ml in accordance with the physiology of the patient.

Figure 6:
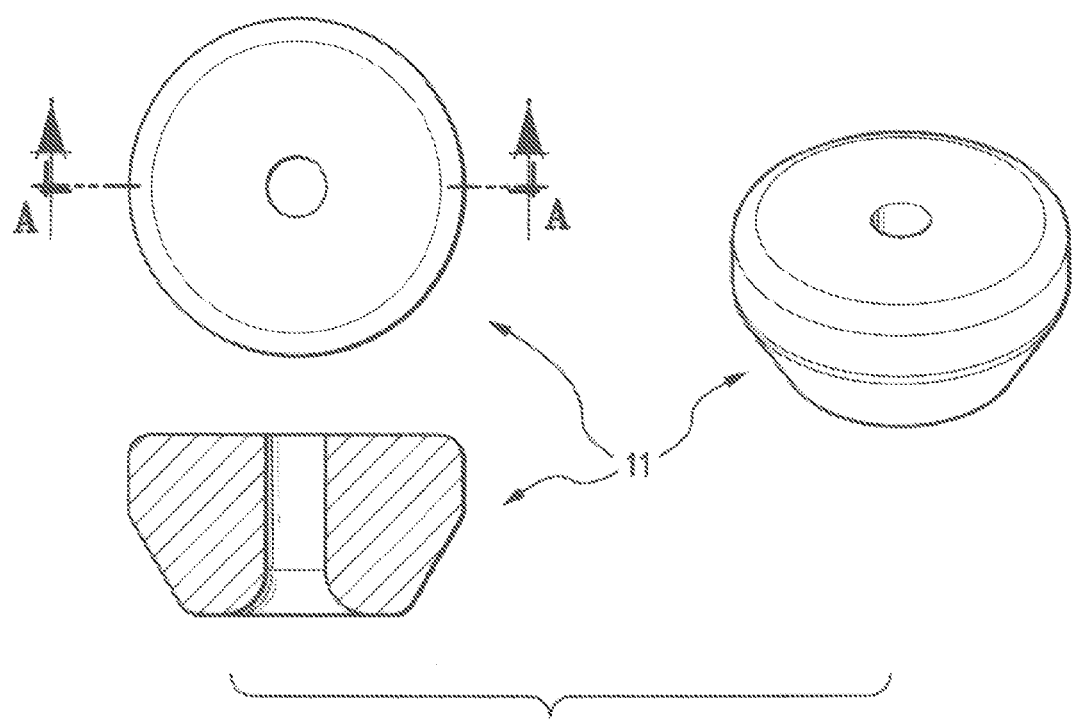
FIG. 6 shows a stop means of the sampling device of FIG. 4 according to some embodiments.

FIG. 6 shows a particularly preferred configuration of the outer sleeve tip which is profiled to locate against the external os of the cervix. In addition, the stop 11 can also be configured to allow more comfortable and precise mating to the external os by providing for partial insertion within the external os and partial abutment thereto, rather than just a simple abutment to the external os.

Figure 7:
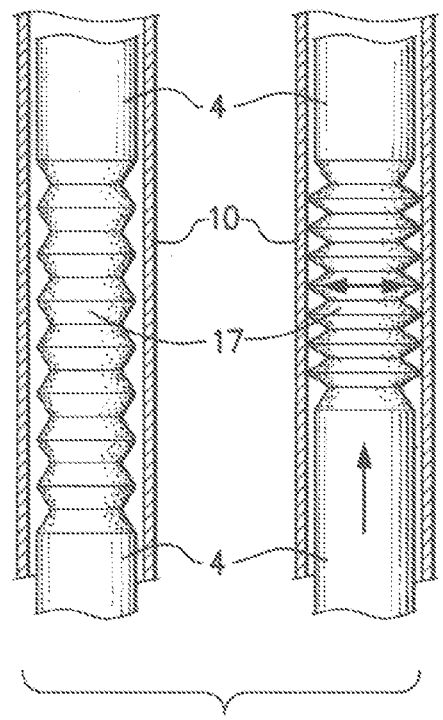
FIG. 7 shows an optional clutch adapted to halt or restrict the telescopic movement of the inner tube relative to the outer tube or sleeve according to some embodiments.

Referring to FIG. 7, the device of the invention may be provided with an optional clutch adapted to halt or restrict the telescopic movement of the inner tube 4 relative to the outer tube or sleeve 10 in the event that the insertion of the inner tube within the cervix of the patient, encounters unexpected resistance. The clutch can take the form of a resilient portion 17 along the length of the inner tube positioned within the confines of the outer tube or sleeve 10 such that attempts to push the inner tube to extend beyond the outer sleeve 10 will be limited or restricted if the sample head of the elongate tube encounters resistance, whereby the resilient means 17 is cause to expand axially and to bear against the inside of the outer sleeve 10 thereby causing resistance and preventing further extension of the inner tube. In this manner, the sampling device of the invention can be provided with the safety feature minimising any unintentional damage or injury that may be occurred if the inner tube encounters unexpected resistance during insertion.

In another aspect the invention provides a method of sampling biological material from a patient which will be described in more detail with reference to FIGS. 5 and 8 to 11.

The methods of the invention comprise the steps of introducing the sampling device into the cervix of a patient whereby the sampling device includes a sampling head positioned at the internal os region of the patient's cervix whereby the sample is taken from the internal os region of the patient and the sampling device subsequently withdrawn from the patient and the collected biological material is then harvested.

Preferably the method of the invention includes the premeasurement of the cervical canal length of the patient by ultrasound or other means, whereby adjustable stop means of the sampling device, as previously described, can be set so as to position the sampling head at or near the internal os region of the patient's cervix. Once the measurements and settings are complete, the device can be inserted into the patient with a stop means gently abutting the external os such that the sampling head is correctly positioned at the internal os whereby the sampling head can be left to absorb the cell sample and most preferably absorb the predetermined quantity of cell sample materials whereby the device can then be removed and the biological material harvested and collected.

Referring to FIG. 5, the methods of the invention preferably utilise the cell sampling device as previously described. Referring now to FIG. 5*a*, the method of the invention includes the step of providing a preliminary measurement of the cervical length of patient by ultrasound or other suitable means. Once the cervical length of the patient is determined and the precise position of the internal os, the sampling device can be adjusted such that the first stop 11 is adjusted such that the outer tube or sleeve 10 is left with a projection through the external os sufficient to allow the sample head 9 to be extended whereby the further reach achieved positioned the sample head 9 at the internal os. Referring now to FIG. 5b the precise extension of the sample head 9 by way of telescopic movement of the elongate tube 4 via the handle 7 is provided by a second stop 12 which allows the sample head 9 to be duly extended into the internal os region once the sampling device has been inserted into the patient with the first stop 11 abutting the external os. In use, in this method of the invention, the device would be inserted into the patient with the elongate tube being retracted such that the sample head 9 is fully protected within the confines of the outer sleeve 10 during the insertion process. In this configuration, the device would be gently inserted into the patient with the protruding portion of the outer sleeve penetrating the external os only so far as the first stop 11 which would then abut the external os so as to provide the preliminary insertion of the device, partially within the cervix of the patient. Once this is achieved, the operator could then gently extend the sample head 9 by moving the handle 7 so as to telescopically extend the elongate tube 4, relative to the outer sleeve 10 so far as the second stop 12 would allow as per FIG. 5b. At that point, the sample head 9 would have been moved out of the confines of the outer sleeve 10 and caused to position itself precisely at the internal os. Once the sample head is positioned at the internal os, it is allowed to remain in position for a predetermined time until the predetermined quantity of sample is fully collected from the internal os region, such that no further sample is capable of being collected.

Figure 8:
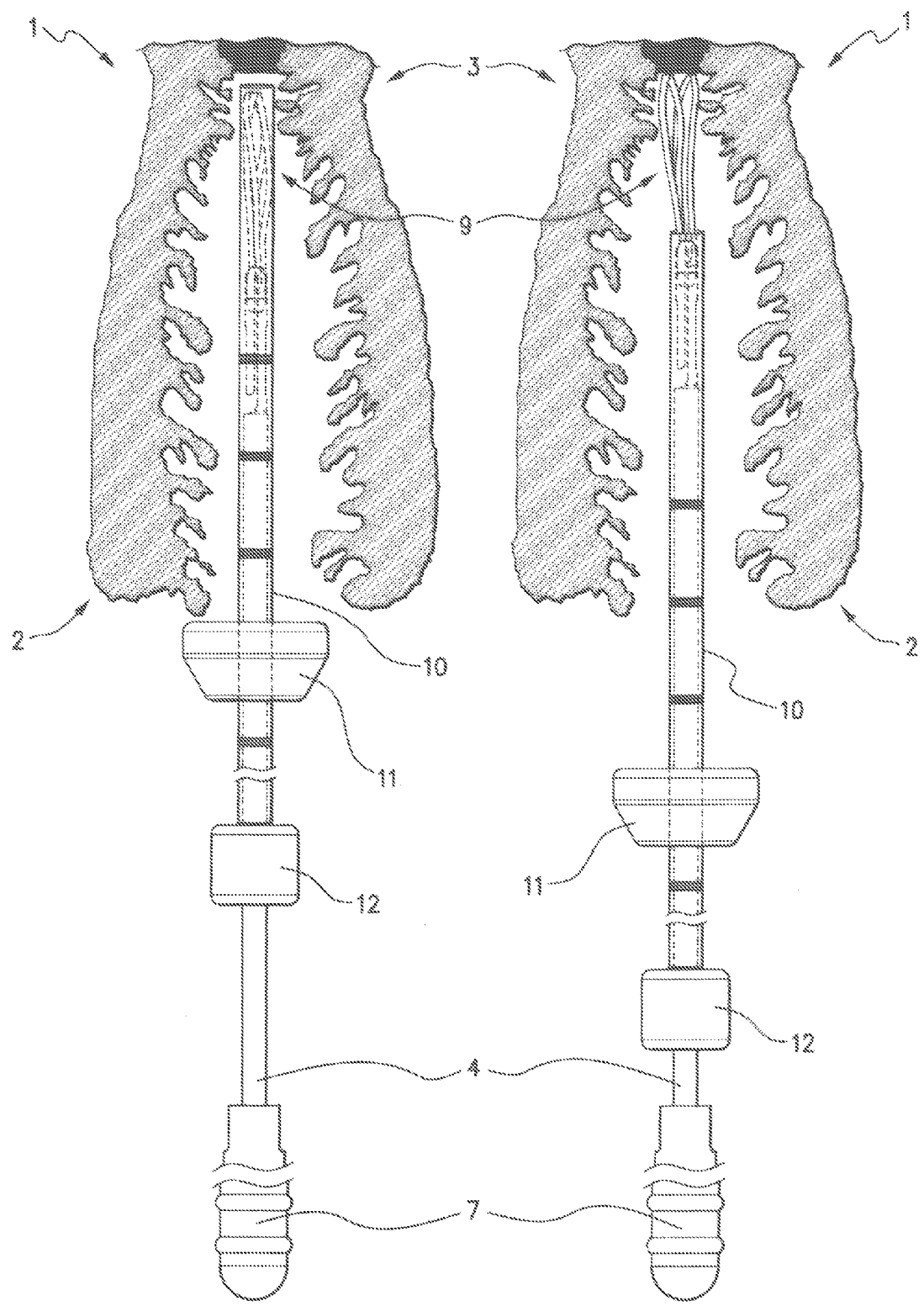
FIG. 8 shows a lengthwise view of the sampling device of FIG. 4 in first and second positions relative to a human cervix.

The methods of the invention can alternatively utilise the device as previously described in a different sampling method as shown in FIG. 8. The sampling methods in this embodiment proceed by setting the first stop 11 along the length of the outer sleeve 10 at such a position that the full extent of the outer sleeve 10 occurs precisely at the internal os position 3 in the patient's cervix 1. The second stop 12 is positioned on the insertion tube 4 so as to position the sample head 9 within the confines of the outer tube 10. Once the sampling device is so set, the device is carefully inserted into the patient's cervix with the stop 11 gently abutting the external os 2. At this stage, the elongate tube 4 is fully extended but such that the sample head is still protected within the confines of the outer tube 10. In this manner, the device of the invention allows for the full protection of the sampling head during entry into the cervix so as to prevent any contamination or sampling from inappropriate regions of the cervix. At this stage, the sample head is ready to be exposed with the exposure accomplished by gently and carefully withdrawing the outer tube 10 relative to the external os and stop 11 ensuring that the elongate tube 4 and sample head 9 remain positioned relative to the internal os. In this manner, the outer tube 10 is gently withdrawn from the sample head 9 allowing the sample head exposure to the internal os for absorption of the cell sample. The device is then left in this position for the appropriate length of time to absorb the predetermined quantity of sample and once the predetermined quantity of sample has been collected, the device can be gently removed and the harvested biological material collected.

In addition to the above, the device of the invention allows the previously described methods to incorporate the use of aspirating systems whereby a simple cylinder and barrel or plunger connected to a separate syringe or alternative vacuum systems, can be incorporated to assist in the suction or removal of cervical mucous if such additional assistance is deemed to be required. In this aspect of the invention, the outer sleeve 10 can form a suitable conduit from the vacuum to the region of the sampling head.

In the aspirating form of the invention, a plunger may be used to push out the sampling head before it is withdrawn to aspirate the sample and a syringe could be temporarily or permanently attached to the device of the invention prior to insertion into the cervix. The syringe may connect via a luer-style fitting to a tube that either temporarily houses or is connected to the absorbent material of the sample head. Alternatively, any other manual pumping device including a fixable tube or bladder could be incorporated in a similar manner. In addition to the above, a powered device could be used to provide suction necessary to aspirate the sample, the powering device could take the form of a pump, it could be used to provide continuous or intimate suction until the desired sample volume is obtained as an alternative to absorbing the sample by passive suction only. Such an option may allow for the repositioning of a device while sampling if the original positioning appears to require adjustment.

The fluid or sample could be aspirated into the tip or barrel of the elongate tube 4 directly or most preferably the tip of the tube could be adapted to protrude beyond the outermost portion of the sampling head and/or remain within or partway through the sample head. The aspirating barrel, which may be incorporated in a function of the outer sleeve and/or elongate tube 4, could be configured to ensure that any fluid aspirated must pass through the sample head. In this manner, the sample head could act as a diffuser for the suction so that whilst advice is capable of aspirating a volume of fluid and mucous, the sponge and passive action of the device as previously described, reduces the aspirating pressure required and/or experienced in any part of the cervical canal during sample collection.

Figure 11:
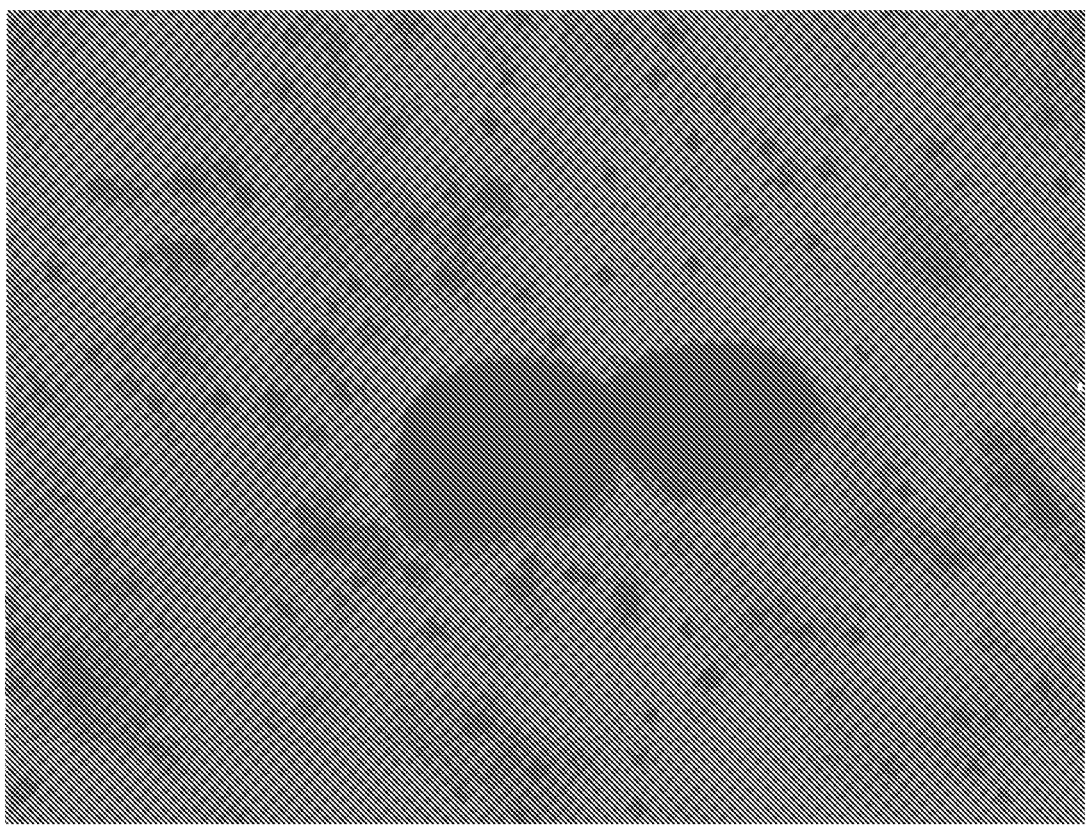
FIG. 11 is an exemplary image of syncytiotrophoblasts that can be isolated using the sampling device of FIG. 4.

FIG. 11 provides an example of syncytiotrophoblasts isolated using the device of the invention. The sample was obtained from at the level of the internal os of a 38 year old human female (referred to as Patient 893) who was about 6-7 weeks pregnant and the cells stained with hematoxylin and eosin staining.

The device of the invention includes many advantages as detailed above and also further includes the advantages whereby the slow absorption rate of the sponge-like sampling head minimises possible rupture of the cervical plug as sometimes occurs during the use of active sampling techniques. The invention minimises such possibilities and accordingly minimises the possibility of infection and complications as a result of such ruptures. In addition, the soft physical features of the sampling head and minimal impact on the user allows a patient to partake in multiple sampling exercises within a short period of time without undue trauma. Furthermore, the gentle nature of the sampling device of the invention allows sampling time to be extended from the expected time required of about 1 to 2 minutes up to 48 hours if this is so required. The particularly gentle nature of the device of the invention allows such use if required.

The device and methodologies of the invention provide for the first time, a highly reliable means and method of obtaining consistent and high quality biological material comprising fetal cells previously only obtainable by more evasive methods as previously described.

Storage, Transport and Processing

Once intact fetal cells are obtained, the sample can be stored at 0 to 4° C. until use to minimize the number of dead cells, cell debris and cell clumps. The sample can be transported and/or stored in HypoThermosol-FRS (HTS-FRS) Medium (Biolife Solutions) at 4° C. For long term storage, the sample can be stored in CryoStor CS5 (Biolife Solutions) at −80° C.

In a further embodiment, the sample is transported and/or stored in Gibco™ AmnioMaxII, Gibco™ AmnioMax C-100, or Gibco™ Keratinocyte-SFM supplemented with 2% fetal bovine serum, heparin (2500 U), hydrocortisone (5 µg/ml), insulin (5 µg/ml), human epidermal growth factor (5 µg/ml), human basic fibroblast growth factor (5 µg/ml), 25 µg/ml gentamycin, 50 ng/ml amphotericin B, 1-2 mmol/L vitamin C (ascorbic acid) or a water soluble analogue of vitamin E (1 mmol/L Trolox). Alternatively, the sample is fixed in alcohol or liquid-based cytology medium; for example "Universal Collection Medium" supplied by Digene Corp. as described in U.S. Pat. No. 6,969,585.

In one embodiment, the transport and/or storage media comprises serum such as bovine calf serum or human serum.

For short term storage, for example a few hours, phosphate buffered saline is sufficient.

In a further embodiment, the storage medium is degassed with nitrogen to reduce oxidative stress to the samples.

In an embodiment, red blood cells are removed from the sample. Red blood cells can be removed using any technique known in the art. Red blood cells (erythrocytes) may be depleted by, for example, density gradient centrifugation over Percoll, Ficoll, or other suitable gradients. Red blood cells may also be depleted by selective lysis using commercially available lysing solutions (eg, FACSlyse™, Becton Dickinson), Ammonium Chloride based lysing solutions or other osmotic lysing agents.

In some instances it is not necessary that intact cells be used for fetal material analysis. In these circumstances it is not essential that steps be taken to keep at least some of the cells alive. For example, the sample, or a portion thereof, can be snap frozen.

Labelling and/or Detection of Fetal Cells

Fetal cells can be positively and/or negatively selected using a variety of techniques well known in the art, including cell sorting, especially fluorescence-activated cell sorting (FACS), by using an affinity reagent bound to a substrate (e.g., a plastic surface, as in panning), or by using an affinity reagent bound to a solid phase particle which can be isolated on the basis of the properties of the solid phase particles for example beads (e.g., coloured latex beads or magnetic particles). Naturally, the procedure used will depend on whether maternal or fetal cells are being selected and how the cells have been labelled.

For selection of cells by cell sorting, the cells are labelled directly or indirectly with a substance which can be detected by a cell sorter, preferably a dye. Preferably, the dye is a fluorescent dye. A large number of different dyes are known in the art, including fluorescein, rhodamine, Texas red, phycoerythrin, and the like. Any detectable substance which has the appropriate characteristics for the cell sorter may be used (e.g., in the case of a fluorescent dye, a dye which can be excited by the sorter's light source, and an emission spectra which can be detected by the cell sorter's detectors).

In flow cytometry, a beam of laser light is projected through a liquid stream that contains cells, or other particles, which when struck by the focussed light give out signals which are picked up by detectors. These signals are then converted for computer storage and data analysis, and can provide information about various cellular properties. Cells labelled with a suitable dye are excited by the laser beam, and emit light at characteristic wavelengths. This emitted light is picked up by detectors, and these analogue signals are converted to digital signals, allowing for their storage, analysis and display.

Many larger flow cytometers are also "cell sorters", such as fluorescence-activated cell sorters (FACS), and are instruments which have the ability to selectively deposit cells from particular populations into tubes, or other collection vessels. In a particularly preferred embodiment, the cells are isolated using FACS. This procedure is well known in the art and described by, for example, Melamed, et al. Flow Cytometry and Sorting Wiley-Liss, Inc., New York, N.Y. (1990); Shapiro Practical Flow Cytometry, 4 ed, Wiley-Liss, Hoboken, N.J. (2003); and Robinson et al. Handbook of Flow Cytometry Methods Wiley-Liss, New York, N.Y. (1993).

The cells can automatically be deposited in collection vessels as single cells or as a plurality of cells, e.g. using a laser, e.g. an argon laser (488 nm) and for example with a Flow Cytometer fitted with an Autoclone unit (Coulter EPICS Altra, Beckman-Coulter, Miami, Fla., USA). Other examples of suitable FACS machines useful for the methods of the invention include, but are not limited to, MoFlo™ High-speed cell sorter (Dako-Cytomation Ltd), FACS Aria™ (Becton Dickinson), ALTRA™ Hyper sort (Beckman Coulter) and CyFlow™ sorting system (Partec GmbH).

For the selection of cells from a sample using solid-phase particles, any particle with the desired properties may be utilized. For example, large particles (e.g., greater than about 90-100 µm in diameter) may be used to facilitate sedimentation. Preferably, the particles are "magnetic particles" (i.e., particles which can be collected using a magnetic field). Typically, maternal cells labelled with the magnetic probe are passed through a column, held within a magnetic field. Labelled cells are retained in the column (held by the magnetic field), whilst unlabelled cells pass straight through and are eluted at the other end. Magnetic particles are now commonly available from a variety of manufacturers including Dynal Biotech (Oslo, Norway) and Miltenyi Biotech GmbH (Germany). An example of magnetic cell sorting (MACS) is provided by Al-Mufti et al. (1999) and U.S. Pat. No. 4,675,286.

Laser-capture microdissection can also be used to select labelled cells. Methods of using laser-capture microdissection are known in the art (see, for example, U.S. 20030227611 and Bauer et al., 2002).

As the skilled person will appreciate, maternal cells can be labelled with one type of label, and fetal cells with another type of label, and the respective cells types selected on the basis of the different labelling. For example, maternal cells can be labelled as described herein such that they produce a fluorescent green signal, and maternal cells can be labelled as described herein such that they produce a fluorescent red signal.

Following enrichment, the cells can be cultured in vitro to expand fetal cells numbers using techniques known in the art. For example culturing in RPMI 1640 media (Gibco).

Uses

Fetal cells comprise the same genetic DNA make up of the somatic cells of the fetus, and hence fetal cells obtained using the methods of the invention can be analysed for traits of interest and/or abnormalities of the fetus using techniques known in the art. Such analysis can be performed on any cellular material that enables the trait, or predisposition thereto, to be detected. Preferably, this material is nuclear DNA, however, at least in some instances it may be informative to analyse mitochondrial DNA, RNA or protein from the isolated fetal cells. Furthermore, the DNA may encode a gene, or may encode a functional RNA which is not translated, or the DNA analysed may even be an informative non-transcribed sequence or marker.

In one preferred embodiment, chromosomal abnormalities are detected. By "chromosomal abnormality" we include any gross abnormality in a chromosome or the number of chromosomes. For example, this includes detecting trisomy in chromosome 21 which is indicative of Down's syndrome, trisomy 18, trisomy 13, sex chromosomal abnormalities such as Klinefelter syndrome (47, XXY), XYY or Turner's syndrome, chromosome translocations and deletions, a small proportion of Down's syndrome patients have translocation and chromosomal deletion syndromes which include Pradar-Willi syndrome and Angelman syndrome, both of which involve deletions of part of chromosome 15, and the detection of mutations (such as deletions, insertions, transitions, transversions and other mutations) in individual genes. Other types of chromosomal problems also exist such as Fragile X syndrome, hemophilia, spinal muscular dystrophy, myotonic dystrophy, Menkes disease and neurofibromatosis, which can be detected by DNA analysis.

The phrase "genetic abnormality" also refers to a single nucleotide substitution, deletion, insertion, micro-deletion, micro-insertion, short deletion, short insertion, multinucleotide substitution, and abnormal DNA methylation and loss of imprint (LOI). Such a genetic abnormality can be related to an inherited genetic disease such as a single-gene disorder (e.g., cystic fibrosis, Canavan, Tay-Sachs disease, Gaucher disease, Familial Dysautonomia, Niemann-Pick disease, Fanconi anemia, Ataxia telengectasia, Bloom syndrome, Familial Mediterranean fever (FMF), X-linked spondyloepiphyseal dysplasia tarda, factor XI), an imprinting disorder [e.g., Angelman Syndrome, Prader-Willi Syndrome, Beckwith-Wiedemann syndrome, Myoclonus-dystonia syndrome (MDS)], or to predisposition to various diseases (e.g., mutations in the BRCA1 and BRCA2 genes). Other genetic disorders which can be detected by DNA analysis are known such as thalassaemia, Duchenne muscular dystrophy, connexin 26, congenital adrenal hypoplasia, X-linked hydrocephalus, ornithine transcarbamylase deficiency, Huntington's disease, mitochondrial disorder, mucopolysaccharidosis I or IV, Norrie's disease, Rett syndrome, Smith-Lemli Optiz syndrome, 21-hydroxylase deficiency or holocarboxylase synthetase deficiency, diastrophic dysplasia, galactosialidosis, gangliosidosis, hereditary sensory neuropathy, hypogammaglobulinaemia, hypophosphatasia, Leigh's syndrome, aspartylglucosaminuria, metachromatic leukodystrophy Wilson's disease, steroid sulfatase deficiency, X-linked adrenoleukodystrophy, phosphorylase kinase deficiency (Type VI glycogen storage disease) and debranching enzyme deficiency (Type III glycogen storage disease). These and other genetic diseases are mentioned in The Metabolic and Molecular Basis of Inherited Disease, 8th Edition, Volumes I, II, III and IV, Scriver, C. R. et al. (eds), McGraw Hill, 2001. Clearly, any genetic disease where the gene has been cloned and mutations detected can be analysed.

The methods of the present invention can also be used to determine the sex of the fetus. For example, staining of the isolated fetal cells with a Y-chromosome specific marker will indicate that the fetus is male, whereas the lack of staining will indicate that the fetus is female.

In yet another use of the invention, the methods described herein can be used for paternity testing. Where the paternity of a child is disputed, the procedures of the invention enable this issue to be resolved early on during pregnancy. Many procedures have been described for parentage testing which rely on the analysis of suitable polymorphic markers. As used herein, the phrase "polymorphic markers" refers to any nucleic acid change (e.g., substitution, deletion, insertion, inversion), variable number of tandem repeats (VNTR), short tandem repeats (STR), minisatellite variant repeats (MVR) and the like. Typically, parentage testing involves DNA fingerprinting targeting informative repeat regions, or the analysis of highly polymorphic regions of the genome such as HLA loci.

Analysis of Fetal Cells

Figure 9:
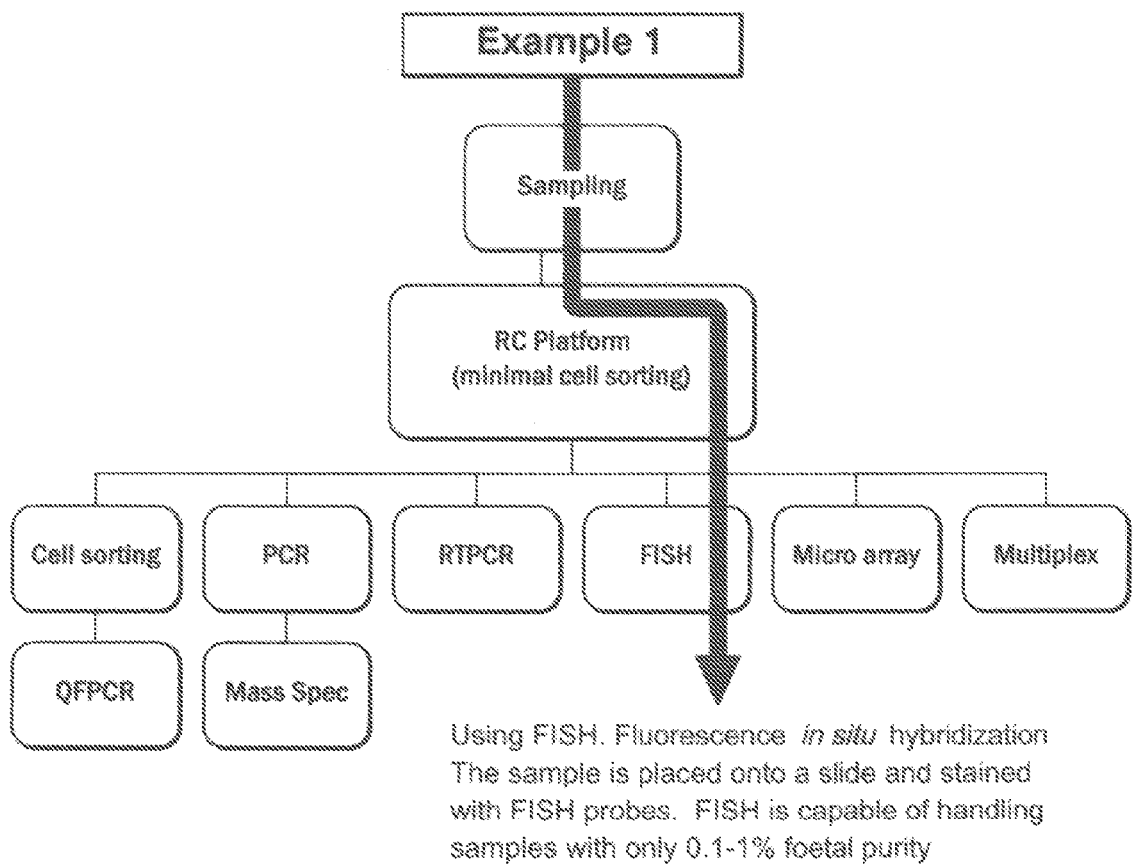
FIG. 9 is a flowchart illustrating various post-platform processes, for example FISH, that can be performed on the sample obtained with a sampling device described herein.
Figure 10:
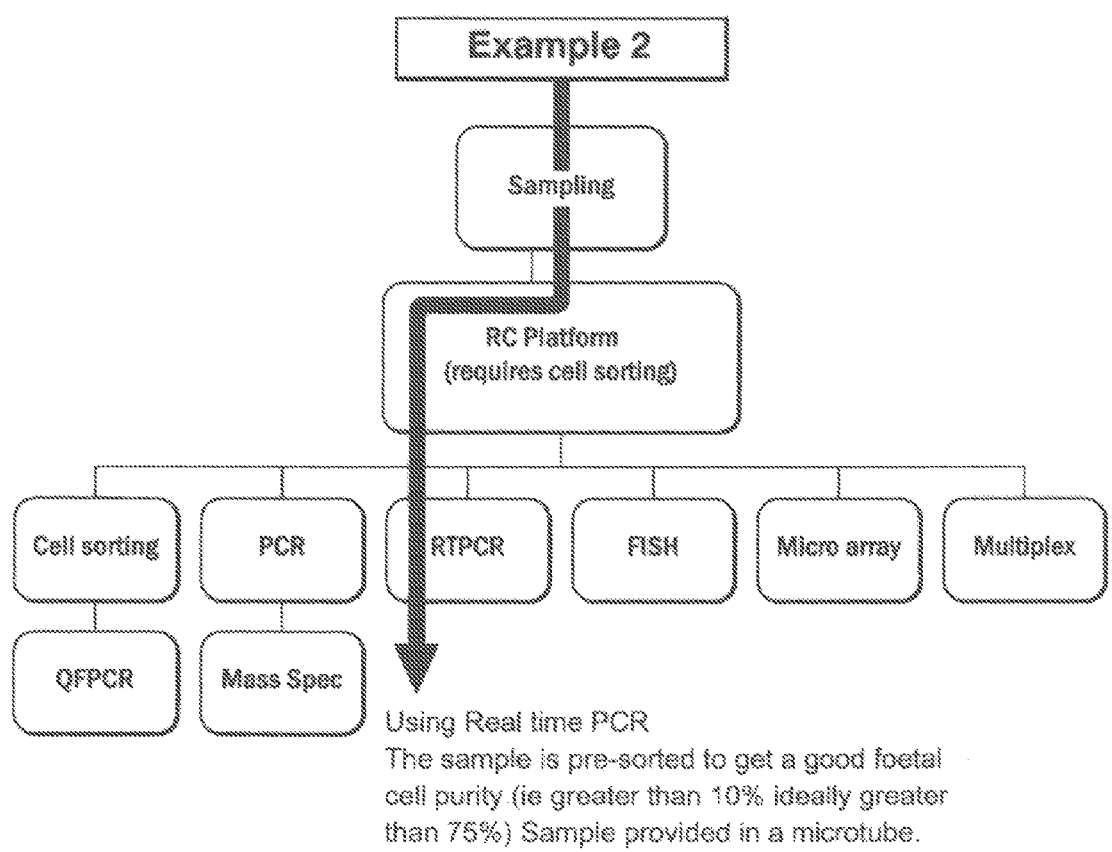
FIG. 10 is a flowchart illustrating various post-platform processes, for example PCR that can be performed on the sample obtained with a sampling device described herein.

Fetal cells enriched/detected using the methods of the invention can be analysed by a variety of procedures, for instance keeping the sample alive or if cell sorting is not required, the sample can be fixed. FIG. 9 shows example 1 using the first post platform process. FIG. 10 shows example 2 using the PCR post platform process. However, typically genetic assays will be performed. Genetic assay methods include the standard techniques of karyotyping, analysis of methylation patterns, restriction fragment length polymorphism assays, sequencing and PCR-based assays (including multiplex F-PCR STR analysis, whole genome amplification and microarray analysis), as well as other methods described below.

Chromosomal abnormalities, either in structure or number, can be detected by karyotyping which is well known in the art such as FISH. Karyotyping analysis is generally performed on cells which have been arrested during mitosis by the addition of a mitotic spindle inhibitor such as colchicine. Preferably, a Giemsa-stained chromosome spread is prepared, allowing analysis of chromosome number as well as detection of chromosomal translocations.

The genetic assays may involve any suitable method for identifying mutations or polymorphisms, such as: sequencing of the DNA at one or more of the relevant positions; differential hybridisation of an oligonucleotide probe designed to hybridise at the relevant positions of either the wild-type or mutant sequence; denaturing gel electrophoresis following digestion with an appropriate restriction enzyme, preferably following amplification of the relevant DNA regions; S1 nuclease sequence analysis; non-denaturing gel electrophoresis, preferably following amplification of the relevant DNA regions; conventional RFLP (restriction fragment length polymorphism) assays; selective DNA amplification using oligonucleotides which are matched for the wild-type sequence and unmatched for the mutant sequence or vice versa; or the selective introduction of a restriction site using a PCR (or similar) primer matched for the wild-type or mutant genotype, followed by a restriction digest. The assay may be indirect, ie capable of detecting a mutation at another position or gene which is known to be linked to one or more of the mutant positions. The probes and primers may be fragments of DNA isolated from nature or may be synthetic.

A non-denaturing gel may be used to detect differing lengths of fragments resulting from digestion with an appropriate restriction enzyme. The DNA is usually amplified before digestion, for example using the polymerase chain reaction (PCR) method and modifications thereof.

Amplification of DNA may be achieved by the established PCR methods or by developments thereof or alternatives such as quantitative PCR, quantitative fluorescent PCR (QF-PCR), multiplex ligation dependent probe amplification, digital PCR, real time PCR (RT-PCR), single cell PCR, restriction fragment length polymorphism PCR (PCR-RFLP), PCR-RFLP/RT-PCR-RFLP, hot start PCR, nested PCR, in situ polonony PCR, in situ rolling circle amplification (RCA), bridge PCR, picotiter PCR and emulsion PCR. Other suitable amplification methods include the ligase chain reaction (LCR), transcription amplification, self-sustained sequence replication, selective amplification of target polynucleotide sequences, consensus sequence primed polymerase chain reaction (CP-PCR), arbitrarily primed polymerase chain reaction (AP-PCR), degenerate oligonucleotide-primed PCR (DOP-PCR) and nucleic acid based sequence amplification (NABSA). Other amplification methods that can be used herein include those described in U.S. Pat. Nos. 5,242,794; 5,494,810; 4,988,617; and 6,582,938.

The acronym "FISH" references a technique that uses chromophore tags (fluorophores) that emit a secondary signal if illuminated with an excitation light to detect a chromosomal structure. FISH uses fluorescent probes which bind only to those parts of the chromosome with which they show a high degree of sequence similarity. Such tags may be directed to specific chromosomes and specific chromosome regions. The probe has to be long enough to hybridize specifically to its target (and not to similar sequences in the genome), but not too large to impede the hybridization process, and it should be tagged directly with fluorophores. This can be done in various ways, for example nick translation or PCR using tagged nucleotides. If signal amplification is necessary to exceed the detection threshold of the microscope (which depends on many factors such as probe labelling efficiency, the kind of probe and the fluorescent dye), secondary fluorescent tagged antibodies or streptavidin are bound to the tag molecules, thus amplifying the signal.

Fetal cells isolated using the methods of the invention can also be analysed using the MassARRAY® and SEQureDx™ procedures of Sequenom Technology (San Deigo, Calif., USA).

Fetal cells obtained using a method of the invention can be placed into wells of a microtitre plate (one cell per well) and analysed independently. Preferably, each cell will not only be screened for a trait(s) of interest, but screened to confirm/detect that the cell in a particular well is a fetal cell. In this instance, multiplex analysis can be performed as generally described by Findlay et al. (1996, 1998 and 2001).

The methods of the invention may include the step of fixing and permeabilizing the cells in the sample. Such procedures are known to those skilled in the art. For example, fixation may involve initial paraformaldehyde fixation followed by treatment with detergents such as Saponin, TWEEN-based detergents, Triton X-100, Nonidet NP40, NP40 substitutes, or other membrane disrupting detergents. Permeabilization may also involve treatment with alcohols (ethanol or methanol). Initial fixation may also be in ethanol. Combined fixation/permeabilization may also be performed using commercially available kits, including DAKO-Intrastain™, Caltag's Fix & Perm reagents, Ortho Diagnostic's Permeafix™. If required, methods for the extraction of DNA from fixed samples for genetic analysis are also known to those skilled in the art. For example, US 20040126796 discloses a method for the extraction of DNA from tissues and other samples, such as formalin-fixed tissue. The isolation of DNA from fixed samples for use in PCR has also been described by Lehman and Kreipe (2001) and Fitzgerald et al. (1993).

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

All publications discussed and/or referenced herein are incorporated herein in their entirety.

The present application claims priority from U.S. 61/147,718 filed 27 Jan. 2009, the entire contents of which are incorporated by reference.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed before the priority date of each claim of this application.

REFERENCES

Adinolphi and Sherlock (1997) Hum Reprod Update. 3: 383-392.
Al-Mufti et al (1999) Am. J. Med. Genet. 85:66-75.
Bauer et al (2002) Int J Legal Med 116:39-42.
Bischoff and Simpson (2006) 18:206-220.
Bulmer et al (1995) Prenat Diagn 15: 1143-1153.
Bussani et al. (2002) Prenat Diagn. 22: 1098-1101.
Bussani et al. (2004) Mol. Diagn. 8:259-63.
Bussani et al. (2007) Mol Diagn Ther. 11:117-121.
Cioni et al. (2003) Prenat Diagn 23: 168-171.
Fejgin et al. (2001) Prenat Diagn. 21: 619-621.
Findlay et al. (1996) Hum Reprod Update 2: 137-152.
Findlay et al. (1998) J Clin Pathol Mol Pathol 51: 164-167.
Findlay et al. (2001) Mol Cellul Endocrinol 183: S5-S12.
Fitzgerald et al. (1993) Biotechniques 15:128-133.
Goldberg et al. (1980) Am J Obstet Gynecol 138:436-440.
Katz-Jaffe et al. (2005) BJOG 112: 595-600.
Lehman and Kreipe (2001) Methods 25:409-418.
Mantzaris et al. (2005) Aus NZ J Obstet Gynaecol. 45: 529-532.
Massari et al. (1996) Hum Genet. 97: 150-155.
Miller et al. (1999) Hum Reprod. 14: 521-531.
Rhine et al. (1975) Am J Obste Gynecol. 122: 155-160.
Rhine et al. (1977) Birth Defects Orig Artic Ser. 13: 231-247.
Rodeck et al. (1995) Prenat Diagn. 15: 933-942.
Shettles (1971) Nature 230: 52-53.
Tutschek et al. (1995) Prenat Diagn 15: 951-960.
Warren et al. (1972) Am J Hum Genet. 24: 22.

The invention claimed is:

1. A sampling device adapted for transcervical sampling of biological materials from a patient comprising:
   an outer tube having visible reference marks at a first end of the tube, the marks indicating intervals of distance along the first end of the tube;
   an elongate insertion member having a first end and a second end, the insertion member being received in and sized to be movable through the outer tube;
   a sampling portion disposed on the first end of the insertion member and configured to collect the biological materials by absorption or adsorption;
   a first stop disposed adjacent the reference marks on the outer tube, the position of the first stop being adjustable with respect to the reference marks on the outer tube; and
   a second stop arranged to limit the distance that the first end of the insertion member can extend past the first end of the outer tube;
   wherein the first stop is sized to pass through a vagina of the patient but to be restricted from passing through an external os of a cervix of the patient, and wherein the outer tube is sized to pass through the external os, and wherein the insertion member is formed of a length to position the sampling portion at an internal os region of the cervix of the patient and to minimize the possibility that a cervical mucus plug of the patient is ruptured.

2. The sampling device of claim 1, wherein the reference marks on the outer tube allow the distance between the position of the first stop and the first end of the tube to be determined.

3. The sampling device of claim 1, wherein the first stop is adjustable to a position that allows the sampling portion of the insertion member to be positioned at the internal os of the patient when the first stop is abutting the external os of the patient and the insertion member has been moved through the outer tube until the second stop has been engaged.

4. The sampling device of claim 1, wherein the first end of the insertion member terminates in a coupling portion and the sampling portion is coupled to the coupling portion.

5. The sampling device of claim 4, wherein the sampling portion comprises a sponge material.

6. The sampling device of claim 5, wherein the sponge material comprises a multi-filamentous array of sponge fingers.

7. The sampling device according to claim 5, wherein the sponge material comprises pores sized between 10 and 2000 microns, with an average pore opening of between 400 and 1000 microns.

8. The sampling device of claim 5, wherein the coupling portion comprises a hook and the sampling portion is retained in the first end of the insertion member by the hook.

9. The sampling device of claim 1, wherein the sampling portion comprises a sponge material.

10. The sampling device of claim 9, wherein the sponge material comprises a multi-filamentous array of sponge fingers.

11. The sampling device of claim 1, wherein the sampling portion comprises a material adapted to expand upon absorption of the biological materials from a dry compressed state to a swollen state.

12. The sampling device according to claim 1, wherein at least one of the insertion member or the sampling portion comprises an ultrasound readable marker to assist in tracing the position of the sampling portion within the patient.

13. The sampling device according to claim 1, wherein the outer tube comprises an ultrasound readable marker to assist in tracing the position of the sampling portion within the patient.

14. The sampling device of claim 1, wherein the sampling portion is adapted for removal from the device and integration with a transport container such that the transport container maintains sterility and integrity of the sampling portion.

15. The sampling device of claim 1, wherein the first stop has an interference fit with the outer tube.

16. The sampling device of claim 1, wherein the sampling portion has a surface area to volume ratio the same as or more than that of a cylindrically shaped sampling portion that would fit within the outer tube.

17. The sampling device of claim 1, further comprising a shield to protect the sampling portion during insertion of at least the sampling portion of the device into the vagina of the patient.

18. The sampling device of claim 17 wherein the shield is a dissolvable chemical coating applied to the outer surface of at least part of the sampling portion.

19. The sampling device of claim 1, wherein the second stop is coupled to the outer tube.

20. The sampling device of claim 1, wherein the second stop is coupled to the insertion member.

21. The sampling device of claim 1, wherein the sampling portion is sized to be movable through the outer tube.

22. The sampling device of claim 21, wherein the insertion member is movable relative to the outer tube to a position in which at least a substantial part of the sampling portion is protected by the outer tube during insertion of at least the sampling portion of the device into the vagina of the patient.

* * * * *